United States Patent [19]

Swann et al.

[11] Patent Number: 4,646,752
[45] Date of Patent: Mar. 3, 1987

[54] ADJUSTABLE INTRACRANIAL PRESSURE MEASURING SCREW

[76] Inventors: Karl W. Swann, 145 Glades Rd., Minot, Mass. 02055; Eric R. Cosman, 872 Concord Ave., Belmont, Mass. 02178

[21] Appl. No.: 488,378

[22] Filed: Apr. 25, 1983

[51] Int. Cl.⁴ .............................................. A61B 5/00
[52] U.S. Cl. .................................. 128/748; 128/774; 33/512; 33/515
[58] Field of Search ............ 128/748, 303 B, 774–775, 128/778; 73/723; 33/511–512, 515

[56] References Cited

U.S. PATENT DOCUMENTS

| 3,938,504 | 2/1976 | Dickinson, III et al. | 128/778 |
| 4,062,354 | 12/1977 | Taylor et al. | 128/748 X |
| 4,186,728 | 2/1980 | Von Lotringen | 128/748 X |
| 4,246,908 | 1/1981 | Inagaki et al. | 128/748 |

FOREIGN PATENT DOCUMENTS

| 2621909 | 12/1977 | Fed. Rep. of Germany | 128/748 |
| 2720455 | 11/1978 | Fed. Rep. of Germany | 128/748 |
| 2384482 | 11/1978 | France | 128/748 |

OTHER PUBLICATIONS

Brock et al.; *Intracranial Pressure*, Subdural Pressure Monitoring in Head-Injured Patients; 1972, pp. 9–13.

Primary Examiner—Lee S. Cohen
Assistant Examiner—Angela D. Sykes
Attorney, Agent, or Firm—Richard J. Birch

[57] ABSTRACT

A screw-type device that can be screwed into a hole in the skull for measuring subarachnoid fluid pressure in the head. The screw-type device has an elongated body with a threaded distal end, and an adjustable depth stop means which can be moved along the distal end of the device and clamped to the body of the device to control the amount of penetration of the distal end into the skull. By this means, the exact placement of the distal tip of the device to the inner table of the skull can be achieved for any skull thickness. A through-opening in the body of the device and connection means at the proximal end enables subarachnoid fluid pressures to be measured by external apparatus. The adjustable depth stop provided added advantages of stability, safety, accuracy, universality and convenience.

3 Claims, 11 Drawing Figures

U.S. Patent  Mar. 3, 1987  Sheet 1 of 2  4,646,752
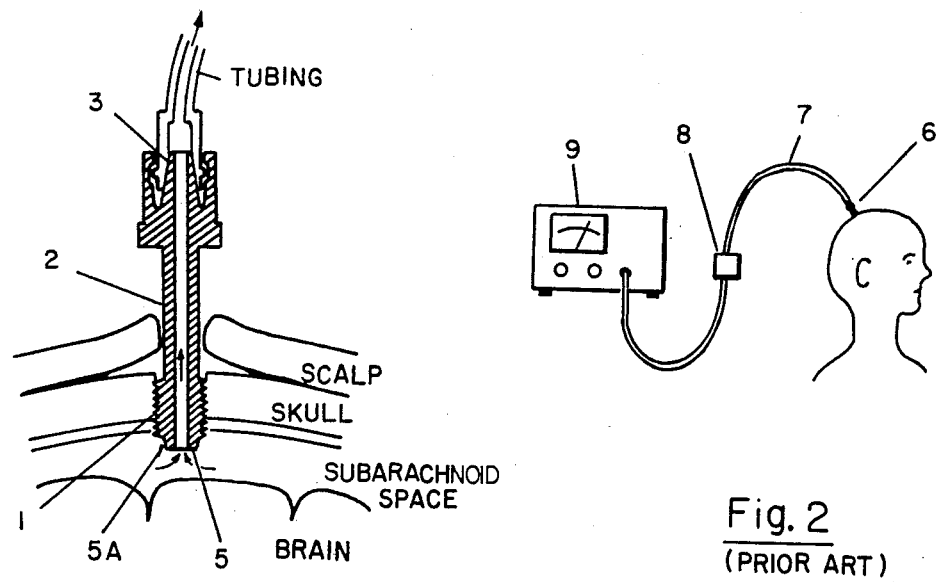
Fig. 1
(PRIOR ART)
Fig. 2
(PRIOR ART)
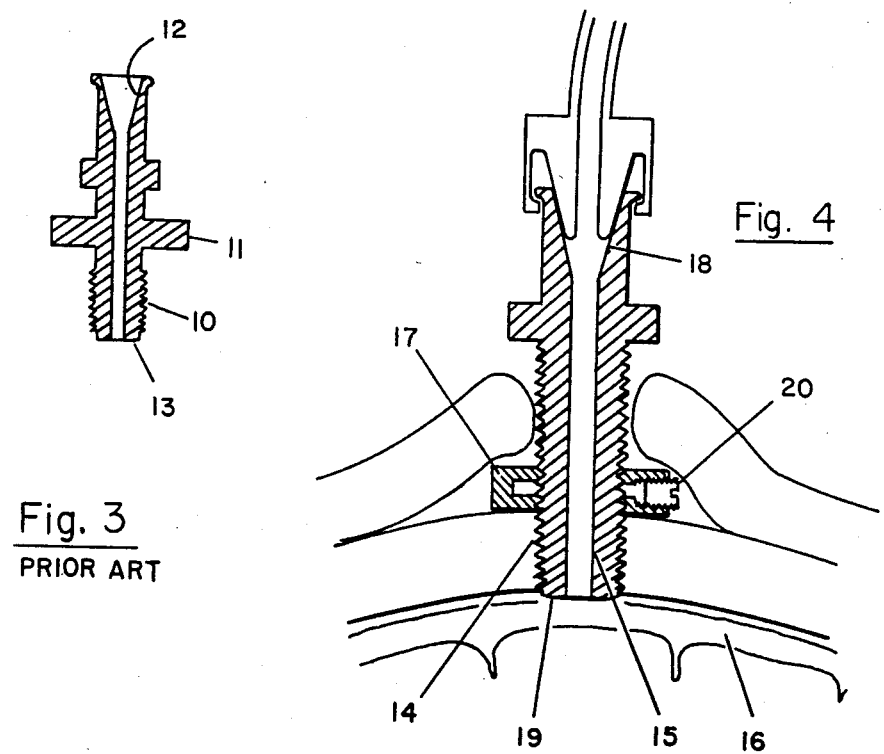
Fig. 3
PRIOR ART
Fig. 4

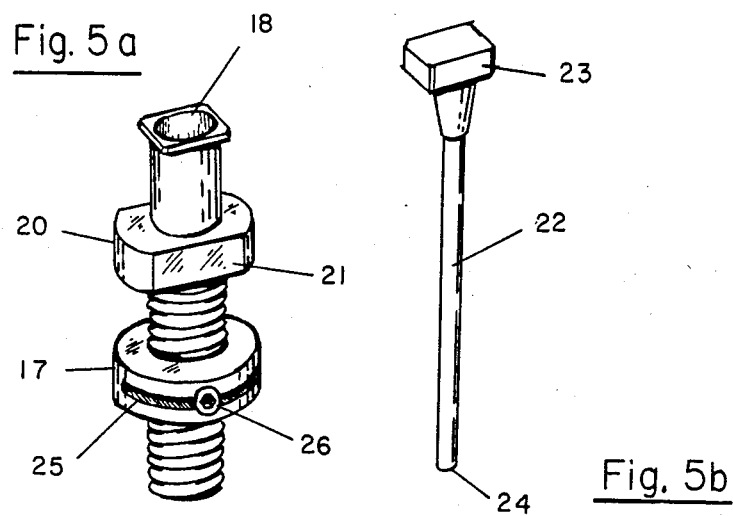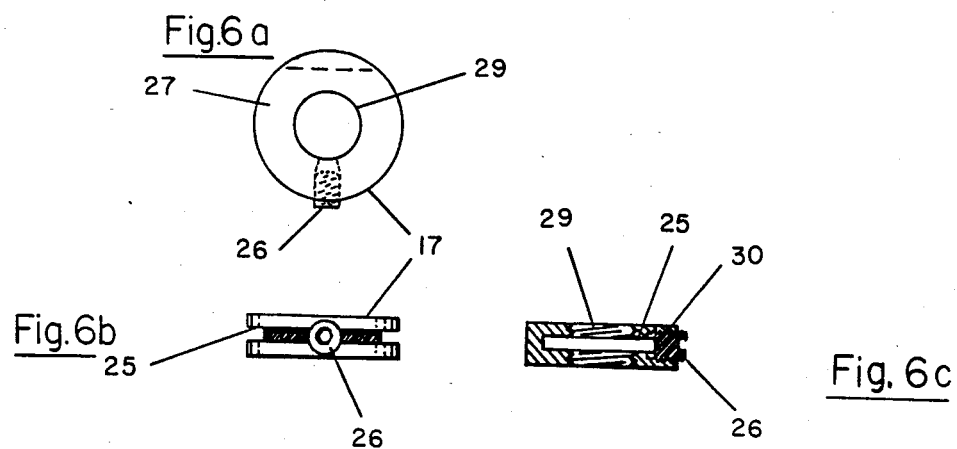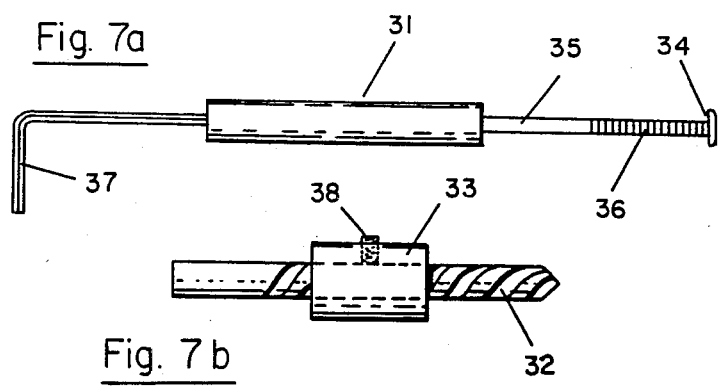

ADJUSTABLE INTRACRANIAL PRESSURE MEASURING SCREW

BACKGROUND OF THE INVENTION

Monitoring of intracranial pressure can be accomplished by several methods. The most widely used techniques involve inserting a catheter in the lateral ventrical or introducing a hollow screw-like device through the skull into the subarachnoid space.

The concept of using hollow screw-like devices to measure and continuously monitor intracranial pressure was introduced in 1971 by Vries and Becker. Their invention is called the "Richmond screw". The basic principle involved in use of a hollow screw device involves providing a fluid connection means from the fluid in the patient's head (the subarachnoid fluid or cerebrospinal fluid (CSF)) to an external pressure sensing system. This is shown schematically in FIG. 2. The screw device screws into the skull and allows CSF to pass through its internal channel to a connection tube and on to a pressure transducer and monitor. The measurement of the fluid pressure then indicates the patient's intracranial pressure (ICP).

The measurement and continuous monitoring of intracranial pressure has been useful clinically. However, the currently used devices can be unstable, do not insure accurate placement of the screw tip in the subarachnoid space, are not designed to prevent accidental plunging of the device through the drill hole into the brain and do not offer the ability to adjust the depth of the screw based on exact measurement of skull thickness and depth of the subarachnoid space.

Another recent design of a screw-like device called the "Philly Bolt" is offered with a fixed flange above its distal threaded portion (FIG. 3). Again since there is no adjustability of the distance from the tip end to flange, exact placement of the tip to the subarachnoid space is often not possible. For this reason, a variety of different lengths of "Philly Bolt" must be available to accomodate different skull thicknesses. Thus this design has the disadvantages of inexact placement of its tip to the subarachnoid space and non-universality of length.

The present invention is a device that is used in the measurement and continuous monitoring of intracranial pressure. The device will be referred to herein as the Swann-Cosman Bolt. It is a screw-type device which can be screwed into a hole in the skull to allow subarachnoid fluid to be coupled to a fluid tubing which in turn is connected to a pressure sensor for measuring the fluid pressure. The device has several novel features which overcome the problems of previous designs.

The basic objectives of this invention are to provide a device that features (1) increased stability within the skull, (2) increased safety with a device to prevent plunging into the brain during and after insertion into the skull, (3) adjustability to the varied skull thicknesses found among patients, (4) the ability to accurately measure the depth of the subarachnoid space with a depth gauge and to place the tip of the device exactly at the desired location, (5) design elements to prevent plugging of the device during insertion such as a metallic stylette and (6) a female luer port that allows the easy attachment of only one stopcock to the device.

The accompanying drawings show examples of prior art and embodiments of the present invention. They illustrate how the invention achieves the above stated advantages and objectives.

BRIEF DESCRIPTION OF THE DRAWINGS

FIG. 1 shows a sectional view of the prior art Richmond Screw;

FIG. 2 shows an example of prior art, the general means by which screw-type devices are used to monitor ICP;

FIG. 3 shows a sectional view of another example of prior art, the Philly Bolt;

FIG. 4 shows a sectional view of an embodiment of the present invention, the Swann-Cosman Bolt;

FIGS. 5a and 5b show another view of the device of FIG. 4 together with its stylet;

FIGS. 6a, 6b and 6c show a detailed view of one embodiment of an adjustable depth stop used with the device of FIG. 4; and, FIGS. 7a and 7b show a set of ancillary devices that can be used with the invention of FIGS. 4, 5 and 6 to enable skull thickness gauging, depth stop locking and skull hole drilling.

Referring to FIG. 1, the Richmond Screw has a threaded tip portion 1, a narrowed shaft section 2 proximal to the threads and a male luer hub 3. Screwing this into the skull provides no depth stop nor any means to accurately gauge how deep the tip end 5 has advanced into the skull.

Referring to FIG. 2, the general connections to a screw-type device 6 are shown. The device acts as an anchor in the skull and a conduit of subarachnoid fluid (CSF) to a tubing 7 which connects to a pressure transducer 8. Thus the CSF fluid pressure is measured directly and monitored on the monitor 9.

FIG. 3 shows the Philly Bolt another screw-type device. It has a threaded distal end 10, a fixed flange 11, and a female luer hub 12. It has no adjustability of the length from flange 11 to tip 13, and thus the tip 13 cannot always be accurately placed relative to the inner table of the skull.

FIG. 4 shows a sectional view of the present invention. It has a threaded distal portion 14, a through-opening 15 for the fluid 16 in the subarachnoid space, a depth stop 17 which can be adjusted on 14, and a female luer hub 18. Stop 17 can be adjusted for a predetermined distance from the distal tip 19 to equal exactly the skull thickness. A lock screw 20, locks 17 relative to 14 once that distance is established.

FIGS. 5a and 5b show an isometric view of the embodiment of FIG. 4. On the hub base 20 there are flat surfaces 21 to accept a wrench for screwing the device into a predrilled hole in the skull. A stylet is also shown having shaft 22 and hub 23, such that when inserted into luer hub 18 the tip 24 of the stylet approximates the tip 19 of the bolt. In the particular embodiment of FIG. 5, the depth stop 17 has a slot 25 parallel to its principal plane and a set screw 26 directed into the slot from the side sack. Thus it expands to two halves of the depth stop when screwed inwards.

FIGS. 6a, 6b and 6c show this in more detail. The depth stop consists of a washer shaped body 27 with a threaded through hole 29 and a slot 25 which is cut part way through it in the plane of the washer. The threaded side hole 30 is a tapered hole which does not penetrate into the side wall so deep as to reach the inner threads 29. In this way, when screw 26 is screwed in, it spreads the portions of the washer above and below the slot 25. When the depth stop washer is threaded into the threads 14 of the bolt, the spread of the washer portion will bind the threads of the washer into the bolt and securely fasten the two together. This provides an effective depth stop for the bolt. This design has the advantage of providing a simple means of clamping the depth stop to the hole and at the same time maintaining the thickness of the depth stop at a minimum and creating a minimal lateral protuberance of the overall depth stop dimension. Depth stop thickness is important so that for a given length of threads 14, one has maximal variation of bolt tip to depth stop distance. Minimal lateral size of the depth stop implies that the size of the scalp incision can be kept small. Clearly, other depth stop designs can be made to give the adjustable bolt capability of the present invention. These might include conventional set screws, lock washers, snap rings, contractable split rings, etc.

FIGS. 7a and 7b show ancillary equipment to the Swann-Cosman Bolt which aid in taking full advantage of its accurate adjustability feature. They are a combined skull depth gauge and depth stop wrench 37 and a drill 32 with depth stop 33. Gauge 31 has one end with a pad 34 on the tip of a rod 35. The rod also has a measuring scale on it. Placing this in a skull hole, one can measure the maximal skull thickness of the hole. Thus the Swann-Cosman Bolt's depth stop can be exactly adjusted so that its tip 19 just reaches the inner table of the skull. The wrench 37 on the other end of 31 is used to tighten the depth of stop screw 26. The drill 32 makes the initial skull hole. The depth stop 33 is fixed to the drill to prevent plunging during drilling. Again set screw 38 is tightened by wrench 37. The skull depth gauge though simple in concept is a unique and novel instrument.

DESCRIPTION OF THE PREFERRED EMBODIMENTS

An elaboration will now be given of how the design features of the Swann-Cosman Bolt and the embodiments of FIGS. 4,5,6, and 7 achieve the objective of the invention stated above.

Stability is a key feature of the invention. Instability can lead to accidental plunging of the device, inaccuracy of pressure measurement and increase the likelihood of disconnection and subsequent contamination. The present invention features a shaft 14 which is the same diameter from top to bottom. This is in contrast to the Richmond Screw (Fig. 1) which has a narrowed proximal portion 2. The narrowing of the Richmond Screw can lead to instability because the twist drill hole is a larger diameter to accomodate the wider threaded area 1. The Richmond Screw also can be quite unstable in the setting of thin skulls (i.e. infants) in part because of a 2.5 mm lip, 5a in FIG. 1, at the bolt tip which has no threads and therefore does not contribute to stability. The Swann-Cosman Bolt features an adjustable depth stop or level lock nut 17 that sits flush with the outer table of the skull and prevents plunging during and after insertion and provides increased stability. The "Philly Bolt" has a fixed collar 11 in FIG. 3 which prevents plunging, but it is not adjustable.

Increased safety on insertion is provided by the Swann-Cosman Bolt. First, a depth measurement gauge 31 of FIG. 7 is utilized to measure the exact thickness of the skull and the location of the subarachnoid space. Secondly, an adjustable level lock nut depth stop 17 can be positioned so the bolt tip 19 stops at the exact measured depth of the subarachnoid space 16. The Richmond Screw has none of the above features. The Philly Bolt has a fixed collar 11 that is not adjustable and therefore does not allow placement of its tip 13 at the varied depths encountered among patients with different skull thicknesses.

Adjustability is another unique and important feature of the Swann-Cosman bolt. No other device combines the ability to measure the exact desired depth of insertion with the ability to adjust a depth stop lock nut 17 that insures placement at the desired depth. This adjustability allows the use of one design in virtually all skull thicknesses from infant to adult. Currently available devices require different design for infants (Philly Bolt) or can be quite unstable in the setting of the thin skull of infants (Richmond Bolt). The adjustable depth stop 17 of the Swann-Cosman Bolt offers essentially an infinite variation of screw device lengths in one universal device. Placing the tip end 19 of the device exactly at the inner table of the skull can be very important because it insures less damage to the brain which may swell up to the skull, because it minimizes chances of occlusion of the through hole 15 with brain or debris, and because it prevents plugging hole 15 with debris or fibrous tissue from the skull hole if the tip 19 is back within the skull hole.

The ability to exactly measure the depth of the subarachnoid space and place the tip of the device at that level is important to maximize accuracy of the system. No previous device includes a depth measurement gauge and an adjustable depth stop lock nut. The subarachnoid space contains cerebrospinal fluid and is the space with which the fluid column within the bolt ideally communicates. Current models do not combine exact measurement and placement of the bolt tip at the level of the subarachnoid space with the ability to do this with one adjustable bolt.

Prevention of plugging of the device by bone chips, blood and brain material is aided by the use of a metallic stylet and by virtue of the ability to place the Swann-Cosman Bolt tip at the exact desired depth without plunging into the brain. Also placement of the bolt tip too high within the twist drill hole could lead to plugging of the device by blood oozing from raw bone edges. The Swann-Cosman Bolt would eliminate this cause of plugging.

A female luer at the proximal end of the Swann-Cosman Bolt allows the use of a single stopcock for attachment of transducer tubing and a flushing syringe. The Richmond Bolt has a male end which requires two stopcocks in tandem. An extra stopcock is undesirable as it increases the bulk of the device and adds more unused ports which increases the potential for contamination.

Other embodiments of the present invention are possible which involve configurational changes in the designs described above, such as various mechanisms and designs for the adjustable depth stop, variations in the threaded portion and hub geometry, variations in the means for measuring the skull thickness, and so. Such variations are intended to be included in the following claims.

What we claim and desire to secure by Letters Patent of the United States is:

1. An apparatus for use in measuring fluid pressure in the skull, said apparatus comprising:
   a generally cylindrical body having a proximal end portion and a corresponding proximal end, a distal end portion and a corresponding distal end;

means defining a fluid pressure communication channel extending through said body from the distal end to the proximal end thereof;

a plurality of screw threads located on the exterior surface of the body at the distal end portion so that the distal end portion of said body can be adapted to be screwed into a skull hole; and, adjustable stop means mounted with respect to the body so that the adjustable stop means can be moved along the distal end portion of the body to establish an adjustable distance between the stop means and the distal end of said body whereby the body can be screwed into a skull hole of a known depth and the stop means can be adjusted beforehand so that the distal end of the body will be located at the level of the inner surface of the skull, said adjustable stop means including a generally planar washer means having:

(i) inner screw threads that cooperatively engage the screw threads on the exterior surface of the distal end portion of the body so that rotation of the threaded washer means varies the distance between the washer means and the distal end of the body; and, (ii) an outer edge and a slot formed therein which extends inwardly from the outer edge of the planar washer means, said slot being parallel to the plane of said generally planar washer means and terminating before reaching said inner screw threads.

2. The apparatus of claim 1 wherein said generally planar washer means includes a tapered, threaded setscrew receiving means located in said generally planar washer means so that when a setscrew is screwed into the setscrew receiving means the washer means slot expands in width to look the washer means against the screw threads located on the exterior surface of the cylindrical body.

3. A combination skull thickness measuring and wrench tool comprising:

a generally cylindrical body adapted for gripping by the operator's fingers;

an allen wrench secured with respect to one end of said generally cylindrical body; and, a skull depth measuring means secured to the other end of said generally cylindrical body, said skull depth measuring means including a shaft with depth indicating markings thereon, said shaft terminating in an outwardly extending pad means adapted to engage the skull.

* * * * *